US012642463B2

(12) United States Patent
Missanelli

(10) Patent No.: US 12,642,463 B2
(45) Date of Patent: Jun. 2, 2026

(54) SYSTEM FOR MONITORING FETAL STATUS DURING CHILDBIRTH

(71) Applicant: Heralife Medical, Inc., Wyndmoor, PA (US)

(72) Inventor: John S. Missanelli, Wyndmoor, PA (US)

(73) Assignee: HeraLife Medical, Inc., Wyndmoor, PA (US)

( * ) Notice: Subject to any disclaimer, the term of this patent is extended or adjusted under 35 U.S.C. 154(b) by 371 days.

(21) Appl. No.: 18/342,143

(22) Filed: Jun. 27, 2023

(65) Prior Publication Data

US 2023/0414138 A1 Dec. 28, 2023

Related U.S. Application Data

(63) Continuation-in-part of application No. 18/299,027, filed on Apr. 11, 2023, now abandoned, which is a
(Continued)

(51) Int. Cl.
*A61B 5/1455* (2006.01)
*A61B 5/00* (2006.01)
(Continued)

(52) U.S. Cl.
CPC .......... *A61B 5/1464* (2013.01); *A61B 5/0205* (2013.01); *A61B 5/14551* (2013.01);
(Continued)

(58) Field of Classification Search
CPC ... A61B 5/1464; A61B 5/1459; A61B 5/1477; A61B 5/1482; A61B 5/0205; A61B 5/14551; A61B 5/14552
See application file for complete search history.

(56) References Cited

U.S. PATENT DOCUMENTS 4,938,218 A 7/1990 Goodman et al.
5,109,849 A 5/1992 Goodman et al.
(Continued)

OTHER PUBLICATIONS

Non Final Office Action issued by the US Patent and Trademark Office in the U.S. Appl. No. 16/540,615 mailed on Sep. 21, 2021, 10 Pages.
(Continued)

*Primary Examiner* — Chu Chuan Liu
(74) *Attorney, Agent, or Firm* — Zaher Li PLLC; Shawn S. Li

(57) ABSTRACT

During childbirth process, trauma to an infant can readily arise, ultimately resulting in fetal hypoxia, academia, and brain damage. Such unfavorable conditions can be prevented by measuring the fetus' blood-oxygen level and heart rate. Without a fetal pulse oximeters, blood oxygen level cannot be monitored non-invasively reliably, which reduces the chance for birth complications to be recognized in time. A noninvasive system to implement such goals and maximize the potential welfare of the fetus may include devices to measure oxygen saturation of hemoglobin (SpO2). Such a device may be an oxy probe that uses a trans-reflective method of SpO2 measurement where oxygen saturation data can be transmitted through wire, fiber optics, and or using a radio frequency link, fetal monitor data can be analyzed, compared to existing data base, and or transmitted via radio waves or internet.

21 Claims, 11 Drawing Sheets

Related U.S. Application Data continuation of application No. 16/540,615, filed on Aug. 14, 2019, now abandoned.

(60) Provisional application No. 63/355,675, filed on Jun. 27, 2022, provisional application No. 63/355,672, filed on Jun. 27, 2022, provisional application No. 63/355,681, filed on Jun. 27, 2022, provisional application No. 63/355,684, filed on Jun. 27, 2022, provisional application No. 63/355,673, filed on Jun. 27, 2022, provisional application No. 63/355,679, filed on Jun. 27, 2022, provisional application No. 63/355,682, filed on Jun. 27, 2022, provisional application No. 63/355,677, filed on Jun. 27, 2022, provisional application No. 62/718,754, filed on Aug. 14, 2018.

(51) Int. Cl.
  *A61B 5/0205*   (2006.01)
  *A61B 5/1464*   (2006.01)

(52) U.S. Cl.
  CPC ........ *A61B 5/4362* (2013.01); *A61B 2503/02* (2013.01); *A61B 2562/0238* (2013.01)

(56)                References Cited

U.S. PATENT DOCUMENTS

| | | | |
|---|---|---|---|
| 5,135,006 | A | 8/1992 | Bellinson |
| 5,782,756 | A | 7/1998 | Mannheimer |
| 5,813,980 | A | 9/1998 | Levinson et al. |
| 6,285,896 | B1 | 9/2001 | Tobler et al. |
| 7,469,158 | B2 | 12/2008 | Cutler et al. |
| 8,417,307 | B2 | 4/2013 | Presura et al. |
| 9,757,058 | B2 | 9/2017 | Ray |
| 10,415,163 | B2 | 9/2019 | Carney |
| 2004/0082842 | A1 | 4/2004 | Lumba et al. |
| 2013/0102863 | A1 | 4/2013 | Aknine |
| 2015/0190063 | A1 | 7/2015 | Zakharov et al. |
| 2015/0282749 | A1* | 10/2015 | Zand ...................... A61B 5/015 600/301 |
| 2018/0103857 | A1* | 4/2018 | Hirmer .............. A61B 5/14552 |
| 2020/0077929 | A1 | 3/2020 | Missanelli et al. |

OTHER PUBLICATIONS

Final Office Action issued by the US Patent and Trademark Office in the U.S. Appl. No. 16/540,615 mailed on Mar. 18, 2022, 9 Pages.

Non Final Office Action issued by the US Patent and Trademark Office in the U.S. Appl. No. 16/540,615 mailed on Dec. 12, 2022, 10 Pages.

International Preliminary Report on Patentability and Written Opinion of the International Searching Authority issued in the PCT Application No. PCT/US2019/0464495 on Feb. 16, 2021, 8 pages.

\* cited by examiner

SECTION A-A
SCALE 1.5 : 1

820    810    800

Extrusion tool can be modified to allow an indentation in the external casing with flexible clip.

Indentation With Clip Assembly

Bottom-up or Top-down view. Indentation on either side.

Lens of Camera

Device Distal Cap at Working End
105

800

USB Connector

Camera is clipped into the Indentation on the casing.

EXAMPLE DISPLAY:

1000

Silicone cap  105

Diodes on
recessed
divider

Positive and
negative power
wires from battery
to diodes glued.

Battery on edge( to
be glued with
biological glue
        1110

Wi-Fi Chip

SYSTEM FOR MONITORING FETAL STATUS DURING CHILDBIRTH

BACKGROUND

Pulse oximeters have conventionally been used to measure the oxygen saturation of arterial blood continuously. To use the pulse oximeters, a probe is attached to the tip of a subject's finger or earlobe, and both red and the probe applies infrared light having different wavelengths to the living body from the probe at given time intervals. The oximeter calculates the oxygen saturation from the ratio between the RED and IR of light absorbance. In a typical case, the red light has a reference wavelength of 660 nm and the infrared light has a wavelength of 900 nm; two light-emitting diodes of these wavelengths and one photodiode for light reception may be contained in the probe.

Although fetal heart monitors can be used as a surrogate means to attempt to measure fetal blood oxygen saturation levels, this method is indirect and thus does not give a fully complete understanding of the fetal status. As a result of this lack of full understanding, emergency medical decisions, such as when to start an emergency caesarean section (C-section) must be made with incomplete knowledge. As a practical matter, doctors sometimes err on the side of caution, which may result in unnecessary C-sections, and the attendant high medical expenses and maternal post-childbirth complications.

Previous attempts to provide this missing fetal blood oxygen saturation levels include the OxiFirst system, produced by Mallinckrodt/Nellcor, now part of Tyco Healthcare. This system, which obtained FDA approval in 2000, works by directly placing the tip of a pulse oximeter sensor up the maternal birth canal, through the cervix, into the uterus, and onto the cheek or temple of the fetus. This method is described in U.S. Pat. Nos. 5,813,980; 5,109,849, 4,938,218 which are incorporated by reference as if fully set forth herein. Unfortunately, due to the high invasiveness and bother of the procedure, the method met with limited medical acceptance in the field, and the manufacturer eventually decided to stop selling the device.

U.S. Pat. No. 5,135,006, which is incorporated by reference as if fully set forth herein, shows a method and apparatus for monitoring the fetus in a birth canal during labor. This fetal monitor probe monitors heartbeat and does not directly measure blood oxygenation.

U.S. Pat. No. 10,415,163, which is incorporated by reference as if fully set forth herein, is based on similar pulse oximetry principal for non-invasive monitoring of fetal blood oxygenation by directing light at the abdomen of a pregnant woman, and detecting light scattered and reflected by fetal and maternal tissues back to the surface of the mother's abdomen. It may not be as accurate because of the distance between the probe and the fetus during delivery.

U.S. Pat. No. 7,469,158, which is incorporated by reference as if fully set forth herein, is also based on a similar pulse oximetry principal for non-invasive monitoring of fetal blood oxygenation but requires it to be screwed in the scalp. It presents a more invasive technology than is desirable.

U.S. Pat. No. 8,417,307, which is incorporated by reference as if fully set forth herein, relates to a transmissive type blood oximeter for measuring the oxygenation. Still, it cannot be used in case of fetal measurements.

Thus, there exists a need for a less invasive, accurate, pulse oximeter with a probe that can accurately and safely measure arterial oxygen saturation of a fetus.

SUMMARY OF THE EMBODIMENTS

During the childbirth process, trauma to an infant can readily arise, ultimately resulting in fetal hypoxia, academia and brain damage. Such unfavorable conditions can be prevented by measuring the fetus' blood-oxygen level and heart rate. Without a fetal pulse oximeters, blood oxygen level cannot be monitored non-invasively reliably, which reduces the chance for birth complications to be recognized in time. A noninvasive system to implement such goals and maximize the potential welfare of the fetus may include devices to measure oxygen saturation of hemoglobin (SpO2) that have been available for at least 50 years. Such a device may be an oxy probe that uses a trans-reflective method of SpO2 measurement where oxygen saturation data can be transmitted through wire, fiber optics, and or using a radio frequency link, fetal monitor data can be analyzed, compared to the existing data base, and or transmitted via radio waves or internet.

DETAILED DESCRIPTION OF THE EMBODIMENTS

Introduction

Figure 5:
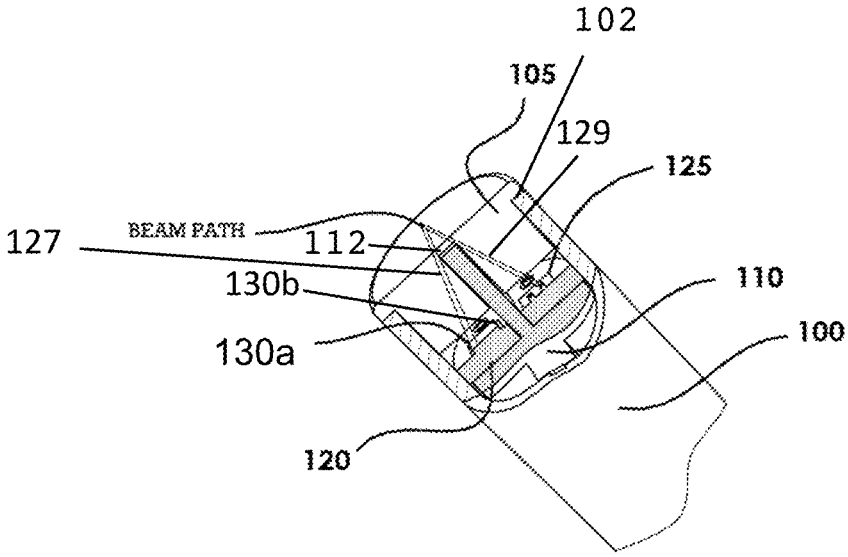
FIG. 5 shows a cut away view of the oxy probe tip illustrating the light path of the reflected light.

The underlying principle of operation is based on the red and infrared light absorption characteristics of oxygenated and deoxygenated hemoglobin. Oxygenated hemoglobin absorbs more infrared light and allows more red light to pass through. Deoxygenated (or reduced oxygen) hemoglobin absorbs more red light, allowing more infrared light to pass through. Red light is in the 640-720 nm wavelength light band. Infrared light is in the 840-920 nm wavelength light band. The embodiment includes a cylindrical housing 100 having two different light sources 130a, 130b, collectively 130 (if a single source), that emit emitted light 127 and a detector or sensor 125 with an opaque partition 110 between sources and detector such a way that the detector 125 will see the reflected light 129 as shown in FIG. 5. The probe 100 may include a clear tip or cap 105 that seals the tip from external fluids and at the same time allows the optical signal/light to be transmitted and received with no to minimal attenuation.

In an alternate embodiment, the probe for measuring hemoglobin oxygenation may require two wavelength emitters, Red (640-720 nm) and IR (840-920). Thus, further emitters may be used in this instance using the same probe configuration in which two other wavelengths can be added. An optional feature for detecting proximity to a fetus may be integrated into the probe.

Detailed Description

The SpO2 monitoring PROBE (called oxy probe herein) may include, as labeled:

100. Probe body or housing
105. Soft clear probe Tip
110. Probe optical divider
115. Probe wire
120. Integrated circuit IC or PC Board
125. Sensor/detector Chip
127. Emitted light
129. Reflected or received light
130a, 130b. Light sources
130. LED Chips
135. Probe Connector
140. Emitter Cavity
145. Sensor Cavity
200. Fetus As shown in FIGS. 1-5, an intra-vaginal and intra-uterine oxy probe 100 allows the arterial oxygen saturation of the fetus 200 to be measured during childbirth process. The oxy probe 100 has a tip 105 that may be made of soft optically clear silicone-type material in its housing and tip 105, which may be safely pressed against the fetus 200 without causing any injury. The tip 105 of the oxy probe 100 is designed to have two optically isolated compartments 140 and 145: One compartment to house the emitters 140 and another to house the sensor 145, wherein the compartments may be separated by an opaque divider 110 that prevents the emitted light 127 from being directly transmitted to the sensor 145. The fetal blood pulse oximetry oxy probe 100 may use at least two wavelengths of the emitted light 127 from a first emitter 130a at about 640 to 680 nm and a second wavelength of light at about 870 to 920 nm 130b, wherein the emitters are preferably LED light emitters. The optically clear oxy probe tip 105 allows the emitted light 127 to illuminate fetal tissue and the sensor 125 can detect the reflected light 129. A CPU remote from tip 105 may perform signal processing to extract the oxygen saturation information related to fetal arterial blood.

The oxy probe may be housed in a housing 100, with dimensions of approximately 0.5 inch in diameter and 2.2-inch-long. A top 0.5 inch of the probe may include the sensor 125, emitters 130, and optical insert 110. These are nominal dimensions and can vary based on requirements, but are chosen to minimize invasiveness to the pregnant woman. The visual divider 110 may be opaque and divide the tip 105 of the probe 100 in two compartments, maintaining the optical isolation between the emitter cavity 140 and sensor 145 cavity (compartments) such that the only way for light to pass between the compartments is through reflection off another surface. The tip of the probe 100 may have a clear, soft, flexible elastomeric material lens 105 that extends into the cavities 140, 145 in such a way as to act as a seal to prevent any fluids from entering the cavities 140, 145 (FIG. 5).

This oxy probe 100 may accommodate additional sensors for monitoring a patient's other conditions, including an arterial hemoglobin oxygen saturation sensor. Most common pulse oximeters used in the hospitals are of transmittance type, whereas the emitters 130a, 130b are placed on one side and the light goes through the tissue to the sensor 125 on the opposite side of the tissue. Alternatively, the emitter 130 and sensor 125 components used in both cases may be similar, with the difference that in the reflective probe, the light reflected by the tissue is compared to light going through the tissue.

Figure 1:
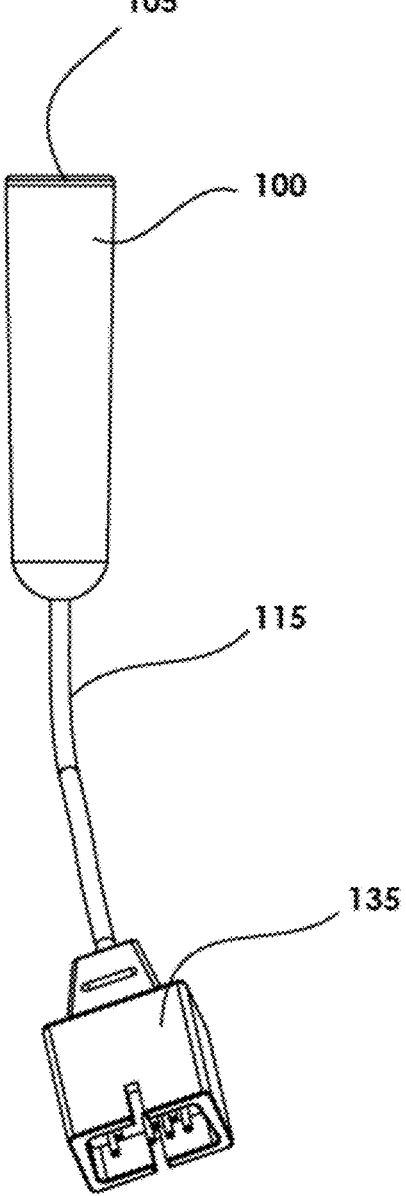
FIG. 1 shows the oxy probe with the connector.
Figure 2:
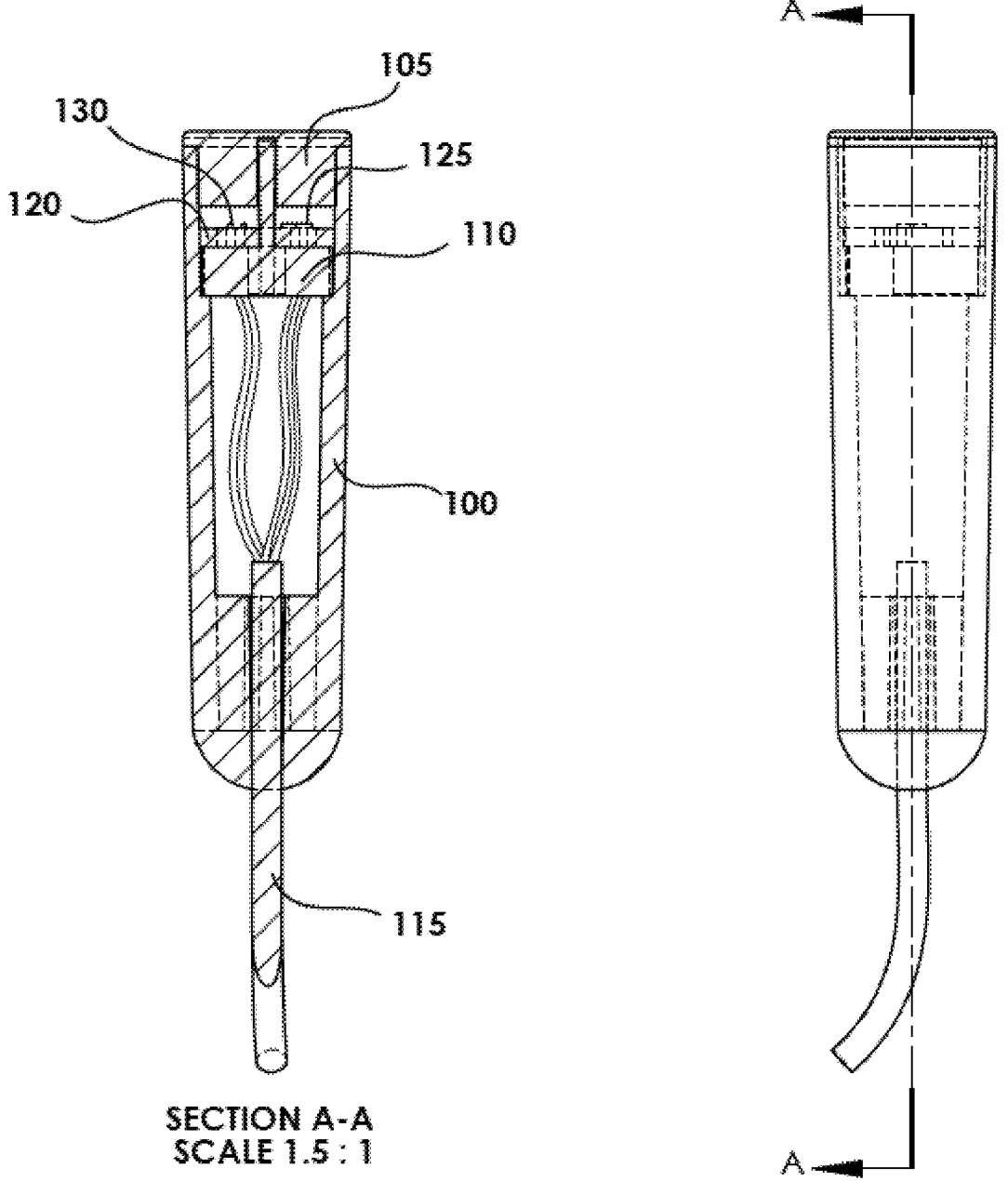
FIG. 2 shows a cross-section A-A of the oxy probe shown in FIG. 1.
Figure 3:
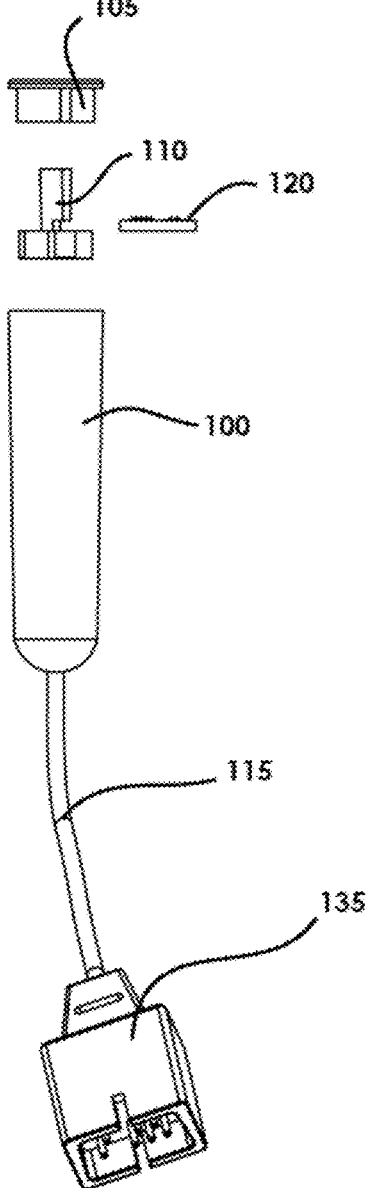
FIG. 3 shows a partially exploded view of the oxy probe and its components.
Figure 4:
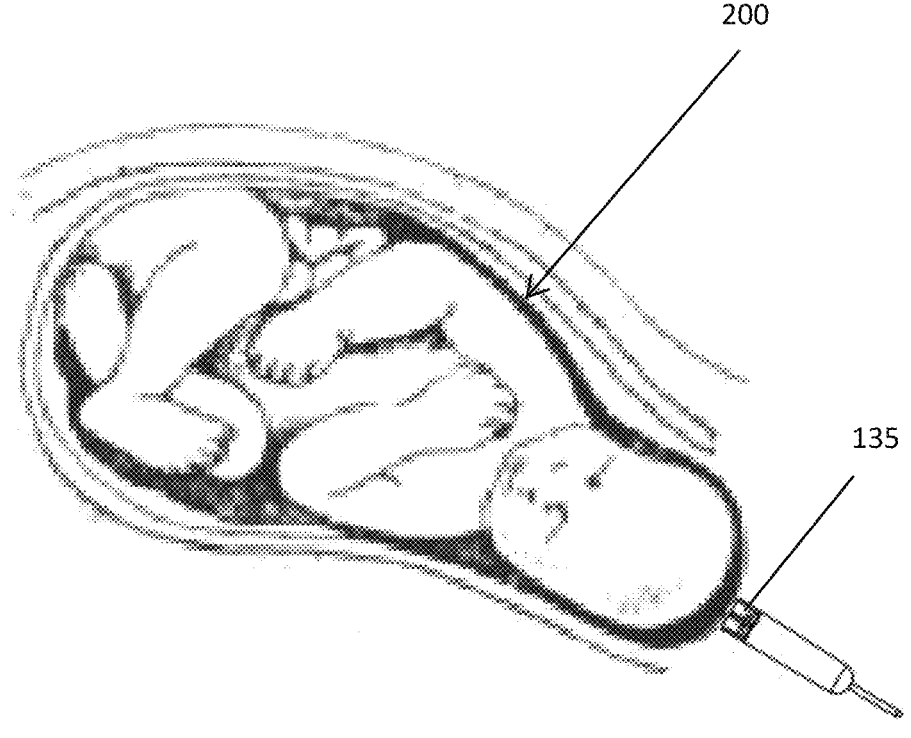
FIG. 4 shows a depiction of the invention in use.

This oxy probe 100 may be used on any location on the body, and it does not have to be pressed against the tissue, for example, close (<1.0 mm) contact with the surface renders accurate data. For monitoring a fetus 200, the oxy probe 100 may be applied through a dilated cervix. The oxy probe 100 may monitor the condition of a fetus 200 during the peripartum process, measuring fetal heart rate, arterial hemoglobin oxygen saturation, electrical activity of the heart, or a combination thereof, by touching the scalp of the fetus 200 (as shown in FIG. 4) or any fetal presenting part.

Figure 6:
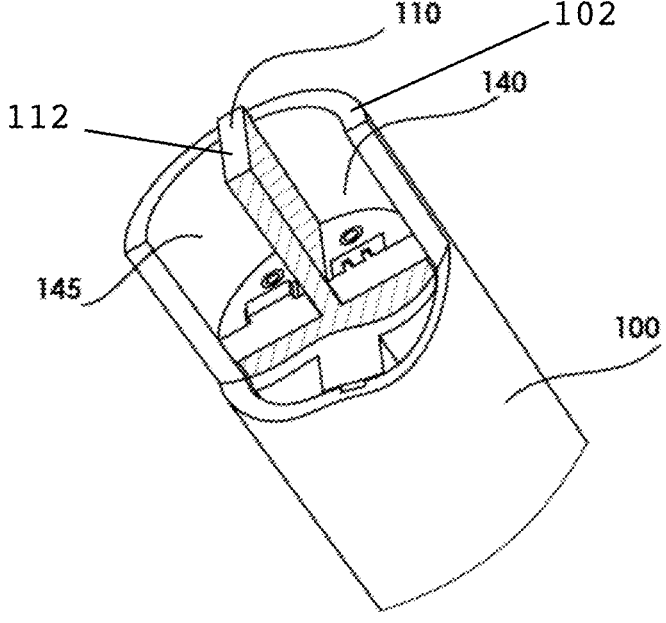
FIG. 6 shows a cutaway view of the oxy probe tip.

The optical divider 110 may be made of an opaque material that prevents transmission of light from reaching the sensor 125 compartment directly from the light source 130. FIG. 6 shows a cutaway view of the oxy probe tip in which it can be appreciated that the divider edge 112 extends to a height higher than the housing edge 102 (FIG. 5 also shows this, but this is harder to appreciate in FIG. 5). The housing 100 of the probe may be made of a light reflecting color such as white.

The probe tip 105, as mentioned above, may be made of optically clear soft silicon or similar materials. This clear tip 105 enables the emitted light 127 from the light source 130 to reach fetal tissue with minimal loss and allows the light to reflect back as reflected light 129 to the sensor 125 efficiently. The tip 105, being soft, also seals the probe tip such that no fluids can reach the emitter 130 and sensor 125. The sealed probe 100 can function properly to obtain accurate readings even on wet surfaces as well as when completely immersed in a fluid.

The light source 130 can include two or more light emitting diodes (LED) configured to emit light at a selected wavelength. When including more emitters, additional emitters may include a third light emitter that emits an emitted light of 550 nm to 620 nm to enable detection of other tissue bio parameters.

The detector 135 may include one or more silicon photodiodes that produce current linearly proportional to the intensity of light striking it. The detector 135 can detect the absorption and/or scattering of the light from the tissue as well as the frequency of the light emitted from the light source 130.

Unlike conventional pulse oximeters, the devices described herein need not be in direct contact with the patient's skin to obtain an accurate, consistent reading due to their being highly directional and having very high gain. As mentioned above, the oxy probe can be positioned 1 mm or less away from the skin surface and still obtain accurate oxygen saturation and heartbeat readings. The probe need not be mechanically coupled to the body to obtain an accurate reading. Because the device need not be in direct contact with the skin and there is no need for mechanical coupling to a patient, the problems that can result including pressure point injuries, pressure necrosis, exsanguinations, discomfort, compression marks, erroneous measurements, infections and other issues caused by direct contact with a device can be avoided.

Shaped Light Sources and Detectors

Figure 7:
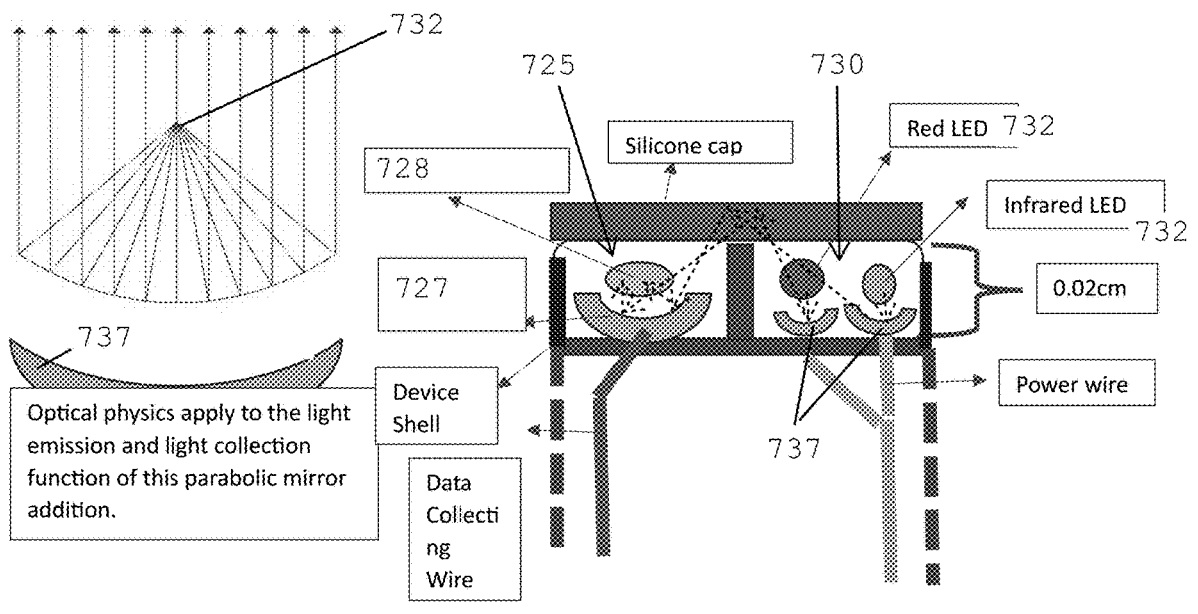
FIG. 7 shows an enhanced light source and collector.

FIG. 7 shows a design with enhanced light sources 730 (red and infrared shown, though others would be possible) and detector/sensor 725. In general, this design operates similarly to the design already discussed, with light emitted from the light source 730 reflecting off tissue and the reflected light collected by the sensor 725.

The change in this design is that each light source 730 and sensor 725 includes a parabolic mirror 737, 727. The light source emitting diode 732 and sensor diode 728 are located in a focal point of each parabolic mirror 737, 727. The emitter mirrors 737 collimate light, which allows for less scatter through the tissues and therefore generates a more powerful reflection. And the reflection collection at the sensor 727 is enhanced when each collecting diode is placed at the focal point of the parabolic collector mirror 727. In use, the emitter LED 732 emits light into the emitter mirror 737 that directs light to the tissue. The sensor mirror 727 collects this reflected light from the tissue and focuses the collected light on the sensor diode 728.

The inset shows a close-up of the light source diode 732 and mirror 737 showing the light collimation. A similar diagram with reversed arrows could be shown for the collector 725.

Oxy Probe with Camera

Figures 8A, 8B:
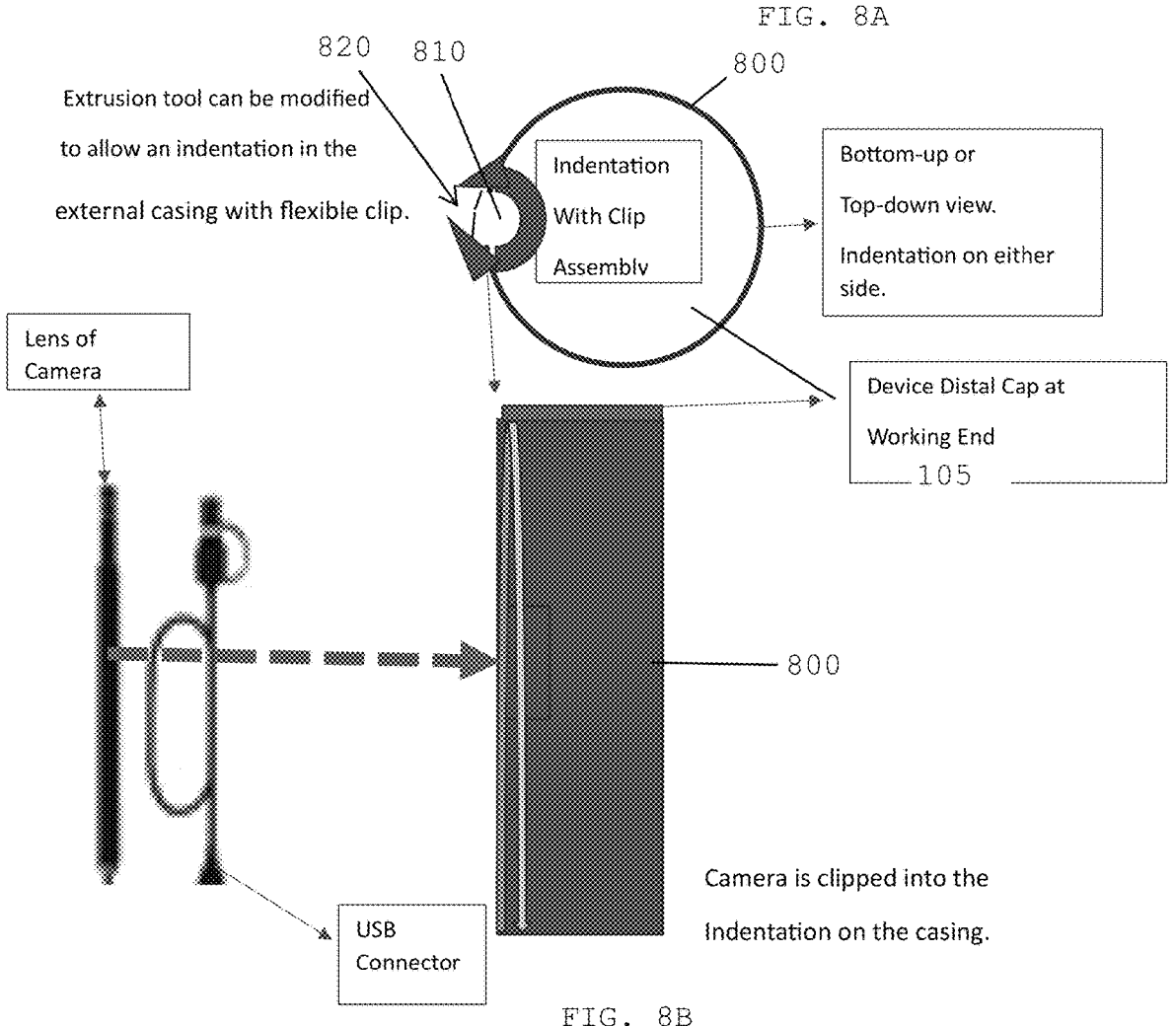
FIGS. 8A and 8B show an embodiment of an oxy probe with an included camera.
Figure 9:
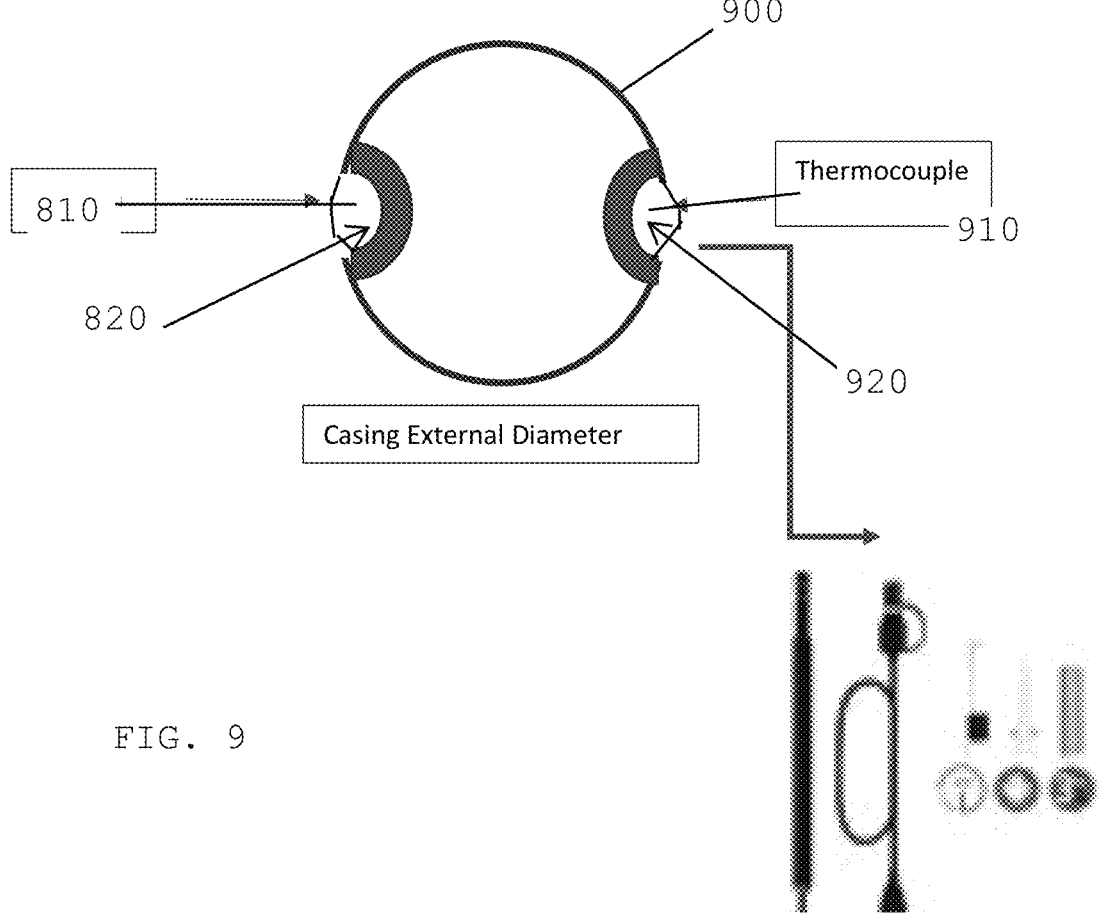
FIG. 9 shows a thermocouple in use with the oxy probe.

A small camera assembly 810 can be added to the external casing 800, which requires modifying the design and manufacturing of the oxy probe as previously described. In this oxy probe generally shown in FIG. 8, the external housing includes a channel or indentation 820 along its length into which a camera 810 can be inserted.

In the obstetrical use of the pulse oximeter, the oxy probe user, usually a doctor, must ensure probe placement on the skin and tissue of the presenting fetal part For some, there may be some difficulty in palpating the uterine cervix and therefore the fetus, and this may result in false positive signals received by the pulse oximeter device. In addition, there is a relatively high incidence of mistaking maternal tissue-reflected light as fetal-reflected light This error may result in dangerous readings.

The camera 810's placement on the pulse oximeter device allows a user, viewing a screen external to the camera and connected thereto in a wired or wireless arrangement, to view precisely what tissue the oxy probe contacts, ensuring an accurate reading during every use thereof.

Oxy Probe with Thermocouple

The physics of temperature and oxygen transport has well established that increasing the temperature of blood results in a reduced affinity of hemoglobin for oxygen and therefore, a rightward shift of the Oxygen-Hemoglobin Dissociation curve. This is necessary in understanding the fetal body and brain temperature differences and the inherent blood-brain protective mechanisms of the fetus. The higher the blood temperature, the more hemoglobin unloads oxygen which leads to hypoxia with obvious consequences to the fetal brain.

The fetus has built-in protection for this risk and can tolerate increased temperatures in the fetal body. The fetal brain blood circulation is kept cooler, inherently, which increases its affinity for oxygen even as the rest of the blood oxygen decreases and ramps up the speed of blood-brain circulation. It has, however, been proven in the sheep in vivo model, that the longer the fetal brain-blood is subjected to heat, the quicker this protective mechanism breaks down. As a consequence the fetal brain circulation loses oxygen, which in turn leads to hypoxia and acidosis.

In an attempt to prevent this, the oxy probe housing 900 may include not only the camera 810 but also similarly in a similar indentation or channel 920, a thermocouple 910. The small, thin thermocouple 910 can be added to an indent 920 of the casing 900 of the pulse ox device, with or without the camera 810, on an ipsilateral side from the camera 810.

The necessary wires to carry power and data may be included within the channels or the housing, or each of the thermocouple and/or camera may communicate wirelessly with displays.

Display for Oxy Probe

Figure 10:
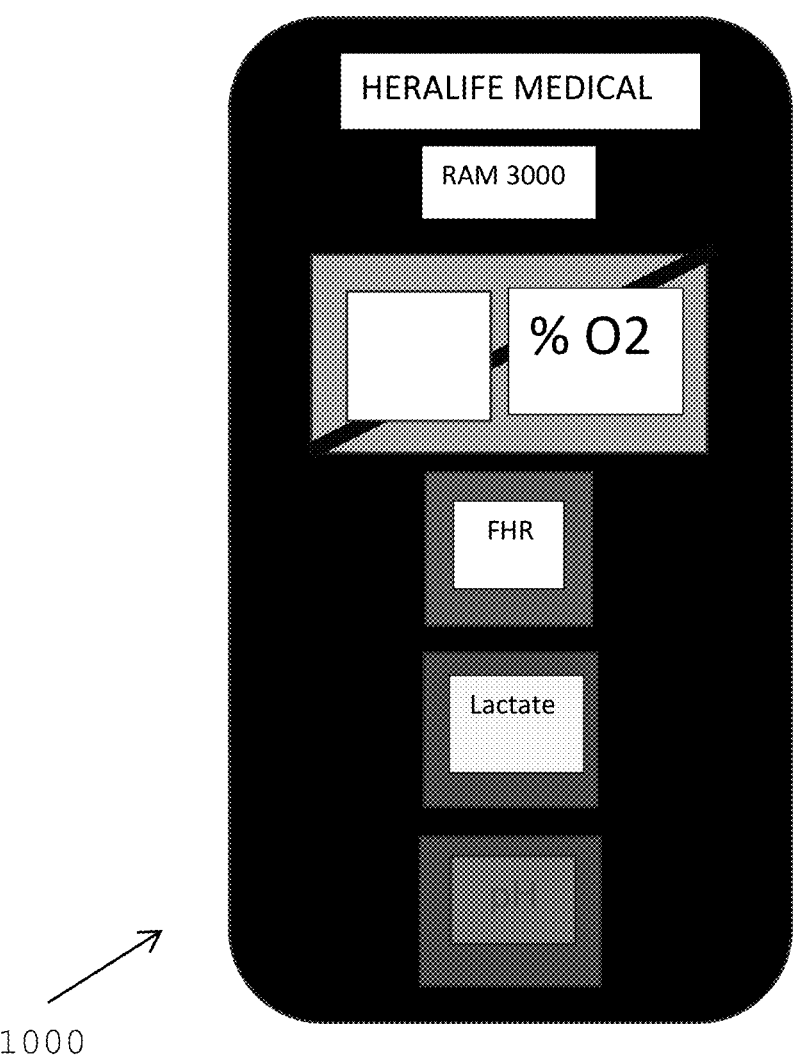
FIG. 10 shows a sample display for the oxy probe.

FIG. 10 shows a sample probe display 1000. The display may be non-disposable, hand-held or stationary, and it receives information from the pulse oximeter and ancillary devices in contact with the display. The data evaluation chip device may be proprietary but can include OEM productions. The display may show fSpO2, temperature, fetal heart rate (FHR), and the blood Lactate and pH as these algorithms become available.

Wireless and Battery

Figure 11:
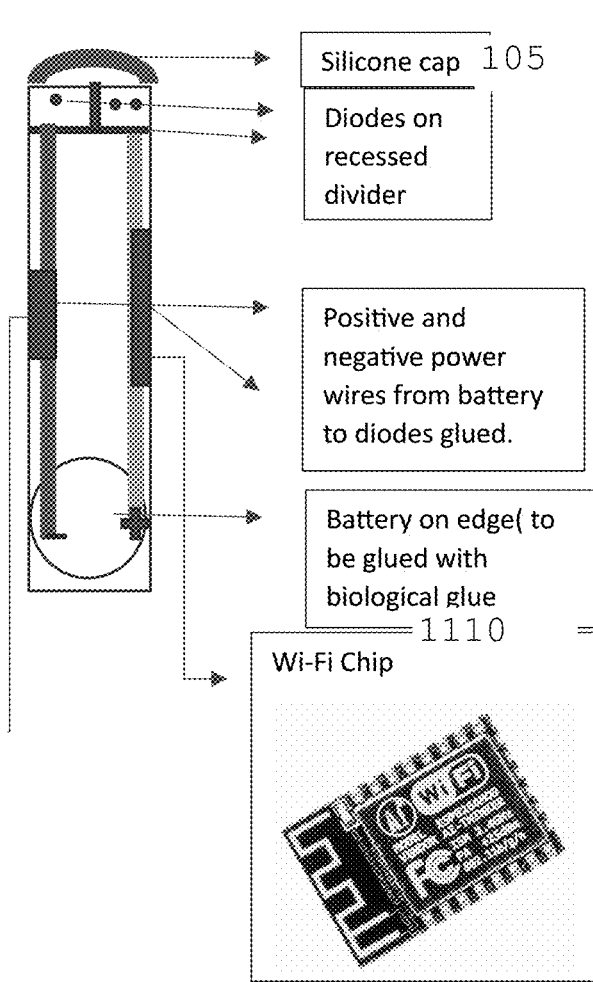
FIG. 11 shows a wireless pulse ox with a battery.

FIG. 11 shows a battery 1110 orientation in the device. The pulse oximeter described herein may be hard-wired to receive power or wireless. With a wireless setup, a battery 1110 would be required. The battery 1110, which may be a flat-round nickel-cadmium type, may be inserted inside the housing end further from the soft cap 105. The battery 1110 may be oriented in parallel with the soft cap surface that contacts the tissue, or in order to reduce the area of the housing, with its longitudinal axis at an orthogonal angle to the longitudinal axis of the housing.

As an aside, the device as shown in FIG. 11 shows the light source and sensors may be oriented on a housing wall.

Other Applications

As already described, this device can be used in any manner of situations for the management of labor and delivery as an accurate oxygen monitor for the fetus.

The pulse ox device may also be used during craniotomy and resection of an area of the brain to detect oxygenation of tissue in apposition to the tissue removed to document that area to be unaffected by the surgery.

The device may further be used in diabetology to determine the accurate oxygenation of the affected areas of the legs, feet, and ankles.

While the invention has been described with reference to the embodiments above, a person of ordinary skill in the art would understand that various changes or modifications may be made thereto without departing from the scope of the claims.

The invention claimed is:

1. An oximeter probe comprising:
   a housing defining a first cavity and a second cavity;
   the first cavity comprising at least two light emitters, wherein each emitter emits an emitted light of a different wavelength than the other of the emitters;
   the second cavity including a detector for detecting both wavelength of reflected light emitted from the at least two light emitters, wherein the reflected light is the emitted light reflected off of tissue; and
   a divider located between the first and second cavities that prevents the emitted light from being directly entering the detector;
   wherein the oximeter probe is in communication with a CPU, which determines oxygen saturation in the tissue based on a difference between the emitted light wavelength and the reflected wavelength;
wherein at least one of the first or second cavities further comprises a mirror that collimates or focuses the emitted or the reflected light;
a camera detachably located within a first channel located longitudinally in the housing:
a thermocouple detachably located within a second channel located longitudinally in the housing.

2. The oximeter probe of claim 1, wherein the at least two light emitters are LED light emitters.

3. The oximeter probe of claim 2, wherein the first cavity further comprises an emitter mirror that collimates the emitted light; and the second cavity further comprises a collector mirror that focuses the reflected light to the detector.

4. The oximeter probe of claim 2, wherein the light emitters include a first light emitter that emits light with a wavelength of 640 nm to 680 nm and a second light emitter emits light with a wavelength of 870 nm to 920 nm.

5. The oximeter probe of claim 3, further comprising a third light emitter that emits an emitted light of 550 nm to 620 nm.

6. The oximeter probe of claim 1, further comprising a transparent cap that allows the emitted light to reach the tissue and receive the reflected light to the detector.

7. The oximeter probe of claim 6, wherein the transparent cap is made from a flexible material.

8. The oximeter probe of claim 7, wherein the flexible material comprises an elastomeric material.

9. The oximeter probe of claim 6, wherein the transparent cap extends into the first and second cavities.

10. The oximeter probe of claim 8, wherein the transparent cap acts as a watertight seal to prevent fluid ingress into the first and second cavities.

11. The oximeter probe of claim 6, wherein the oximeter probe is configured to measure the oxygen saturation in the tissue from a distance.

12. The oximeter probe of claim 11, wherein the distance is less than 1 mm.

13. The oximeter probe of claim 1, wherein the housing is about 0.5 inches in diameter.

14. The oximeter probe of claim 1, wherein the housing is about 2.2 inches long.

15. The oximeter probe of claim 1, wherein the detector comprises silicon photodiodes that produce current linearly proportional to an intensity of the reflected light received at the detector.

16. The oximeter probe of claim 1, wherein the detector detects absorption and/or scattering of the reflected light from the tissue.

17. The oximeter probe of claim 1, further comprising a battery located within the housing, wherein the battery is generally disc-shaped and oriented such that a longitudinal axis of the battery is orthogonally oriented with respect to a longitudinal axis of the housing.

18. A method for detecting oxygen saturation in a fetus comprising:
providing an oximeter probe comprising: a housing defining a first cavity and a second cavity;
the first cavity comprising at least two light emitters, wherein each emitter emits an emitted light of a different wavelength than the other of the emitters;
the second cavity including a detector for detecting both wavelength of reflected light emitted from the at least two light emitters, wherein the reflected light is the emitted light reflected off of fetal tissue;
wherein at least one of the first or second cavities further comprises a mirror that collimates or focuses the emitted or the reflected light; and
a divider located between the first and second cavities that prevents the emitted light from directly entering the detector;
a camera detachably located within a first channel located longitudinally in the housing;
a thermocouple detachably located within a second channel located longitudinally in the housing;
placing the oximeter in proximity to the fetus;
determining, using a CPU, oxygen saturation in the fetus based on a difference between the emitted light wavelength and the reflected wavelength.

19. An oximeter probe comprising:
a housing defining a first cavity and a second cavity;
the first cavity comprising at least two light emitters, wherein each emitter emits an emitted light of a different wavelength than the other of the emitters;
the second cavity including a detector for detecting both wavelength of reflected light emitted from the at least two light emitters, wherein the reflected light is the emitted light reflected off of tissue; and
a divider located between the first and second cavities that prevents the emitted light from directly entering the detector;
wherein the oximeter probe is in communication with a CPU, which determines oxygen saturation in the tissue based on a difference between the emitted light wavelength and the reflected wavelength;
wherein at least one of the first or second cavities further comprises a mirror that collimates or focuses the emitted or the reflected light;
wherein the housing further comprising a first longitudinal channel in an exterior wall of the housing configured to accommodate a camera;
wherein the housing further comprising a second longitudinal channel in the exterior wall of the housing configured to accommodate a thermocouple.

20. The oximeter probe of claim 19, further comprising a camera detachably located within the first longitudinal channel in the housing.

21. The oximeter probe of claim 19, further comprising a thermocouple detachably located within the second longitudinal channel in the housing.

* * * * *